(12) United States Patent
Black et al.

(10) Patent No.: US 8,148,406 B2
(45) Date of Patent: Apr. 3, 2012

(54) POLYMORPH OF N,N-DIETHYL-4-(3-FLUOROPHENYL-PIPERIDIN-4-YLIDENE-METHYL)-BENZAMIDE HYDROCHLORIDE SALT

(75) Inventors: Simon Nicholas Black, Macclesfield (GB); Steve Cook, Wilmington, DE (US); Louis Joseph Diorazio, Macclesfield (GB); James Hulsizer, Wilmington, DE (US); Gary Moore, Wilmington, DE (US); Kathryn Quigley, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 916 days.

(21) Appl. No.: 11/575,841

(22) PCT Filed: Oct. 5, 2005

(86) PCT No.: PCT/SE2005/001469
§ 371 (c)(1),
(2), (4) Date: Jul. 31, 2008

(87) PCT Pub. No.: WO2006/041381
PCT Pub. Date: Apr. 20, 2006

(65) Prior Publication Data
US 2009/0005414 A1    Jan. 1, 2009

(30) Foreign Application Priority Data

Oct. 13, 2004 (SE) ................................. 0402485

(51) Int. Cl.
*A61K 31/4465* (2006.01)
*C07D 211/00* (2006.01)
(52) U.S. Cl. ........................... 514/331; 546/234
(58) Field of Classification Search .................. None
See application file for complete search history.

(56) References Cited

U.S. PATENT DOCUMENTS

| | | | |
|---|---|---|---|
| 2,898,339 A | 8/1959 | Wheeler et al. | |
| 4,581,171 A | 4/1986 | Kennis et al. | |
| 4,816,586 A | 3/1989 | Portoghese | |
| 4,939,137 A | 7/1990 | Russell et al. | |
| 5,140,029 A | 8/1992 | Kennis et al. | |
| 5,574,159 A | 11/1996 | Chang et al. | |
| 5,683,998 A | 11/1997 | Shibayama et al. | |
| 6,187,792 B1 | 2/2001 | Delorme et al. | |
| 6,455,545 B2 | 9/2002 | Delorme et al. | |
| 6,693,117 B2 | 2/2004 | Delorme et al. | |
| 2004/0171612 A1 | 9/2004 | Delorme et al. | |

FOREIGN PATENT DOCUMENTS

| | | |
|---|---|---|
| WO | 9315062 A1 | 8/1993 |
| WO | 9723466 A1 | 7/1997 |
| WO | 9828275 A1 | 7/1998 |
| WO | 9933806 A1 | 7/1999 |
| WO | 0174804 A1 | 10/2001 |
| WO | 0174806 A1 | 10/2001 |
| WO | 0248122 A2 | 6/2002 |
| WO | 2004101522 A1 | 11/2004 |

OTHER PUBLICATIONS

Morissette et al. "High-throughput crystallization: polymorphs, salts, co-crystals and solvates of pharmaceutical solids." Advanced Drug Delivery Reviews, 2004, 56, 275-300.*
Vippagunta, Sudha R. "Crystalline Solids." Advanced Drug Delivery Reviews 48(2001): 3-26.*
Barber et al., "Antinociceptive Effects of the 5-HT2 Antagonist Ritanserin in Rats: Evidence for an Activation of Descending Monoaminergic Pathways in the Spinal Cord," Neurosci. Letters, 1989, vol. 99, pp. 234-238.
Bilsky, et al., "SNC 80, a Selective, Nonpeptidic and Systemically Active Opioid Delta Agonist," J. Pharmacol. Experi. Ther., 1995, vol. 273, pp. 359-366.
Greene, "Protective Groups in Organic Synthesis," Wiley & Sons, 1982, pp. 218-220, 232, 233, 251.
Takemori, et al., "Selective Natrexone-Derived Opinoid Receptor Agonists," Annu. Ref. Pharmacol. Toxicol., 1992, vol. 32, pp. 239-269.
Wei, Z. et al., "N,N-Diethyl-4-(phenylpiperidin-4-ylidenemethyl)benzamide: A Novel, Exceptionally Selective, Potent alpha Opioid Receptor Agonist with Oral Bioavailability and Its Analogues," J. Med. Chem., 2000, vol. 43, pp. 3895-3905.
Zhang et al., "Probes for Narcotic Receptor Mediated Phenomena. 26. 1-3 Synthesis and Biological Examiner of Diarylmethylpiperazines and Diarylmethylpiperidines as Novel, Nonpeptidic Delta Opioid Receptor Ligands," J. Med. Chem., 1999, vol. 42, pp. 5455-5463.
International-Type Search Report issued for SE 0402485-7 on Apr. 15, 2005.
International Search Report issued for PCT/SE2005/001469 on Dec. 20, 2005.
Caira, "Crystalline Polymorphism of Organic Compounds," Topics in Current Chemistry, 1998, pp. 163-208, vol. 198, Springer Verlag Berlin Heidelberg.
Extended European search report issued for 05789875.1 on Apr. 14, 2010.

* cited by examiner

*Primary Examiner* — Rebecca Anderson
*Assistant Examiner* — Alicia L Otton
(74) *Attorney, Agent, or Firm* — Kenneth F. Mitchell

(57) ABSTRACT

Polymorphs of N,N-diethyl-4-(3-fluorophenyl-piperidin-4-ylidene-methyl)-benzamide hydrochloride salt, methods of making these polymorphs and uses thereof are described.

12 Claims, 7 Drawing Sheets

| Polymorph A H($T_1$) | Polymorph B H($T_1$) |
|---|---|
| 2.6 sec. | 7.9 sec. |

| Polymorph A $^{19}$F($T_1$) | Polymorph B $^{19}$F($T_1$) |
|---|---|
| ~20 sec. | ~40 sec. |

FIG. 3

POLYMORPH OF N,N-DIETHYL-4-(3-FLUOROPHENYL-PIPERIDIN-4-YLIDENE-METHYL)-BENZAMIDE HYDROCHLORIDE SALT

CROSS-REFERENCE TO RELATED APPLICATIONS

This application is a US National Stage under 35 U.S.C §371 of International Application No. PCT/SE2005/001469, filed Oct. 5, 2005, which claims priority under 35 U.S.C. §119(a)-(d) to Swedish Application No. 0402485-7, filed Oct. 13, 2004.

FIELD OF THE INVENTION

The present invention relates to polymorphs of N, N-diethyl-4-(3-fluorophenyl-piperidin-4-ylidene-methyl)-benzamide hydrochloride, preparation thereof and uses thereof.

BACKGROUND OF THE INVENTION

Delta receptors have been identified as having a role in many bodily functions such as central nerve and pain systems. Delta agonists have shown many therapeutic activities towards pain, anxiety, depression and other central nerve and pain related symptoms.

U.S. Pat. No. 6,187,792 to Delorme et al. describes some delta agonists that are useful in treating pain and central nerve related diseases. However, there is a still need for improved methods of preparing these compounds and new polymorphs of these compounds.

BRIEF DESCRIPTION OF THE DRAWINGS

FIG. 3 illustrates the relaxation times of $^1H$ and $^{19}F$ of Polymorphs A and B.

DESCRIPTION OF THE EMBODIMENTS

Figure 1:
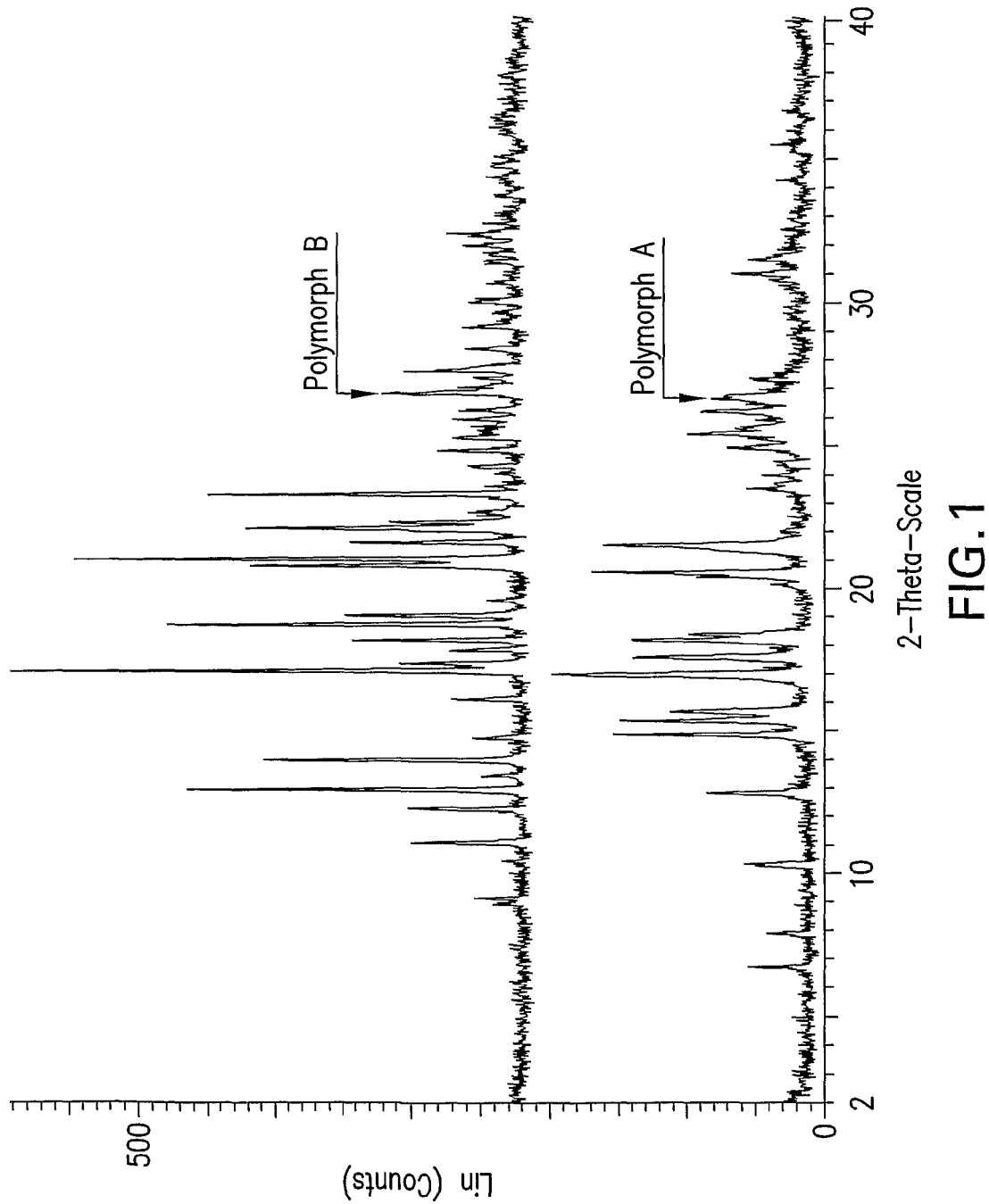
FIG. 1 shows the X-Ray Diffraction Diagram of Polymorphs A and B.

"Ambient temperature" generally refers to a temperature between 0° C. and 100° C. Particularly, "ambient temperature" refers to a temperature between 20° C. and 40° C. More particularly, "ambient temperature" refers to a temperature between 25° C. and 30° C.

Generally, N,N-diethyl-4-(3-fluorophenyl-piperidin-4-ylidene-methyl)-benzamide hydrochloride salt may be prepared according the method described in U.S. Pat. No. 6,187,792 to Delorme et al. (hereafter "Delorme et al."), which is incorporated by reference herein for its description of methods of making and using N,N-diethyl-4-(3-fluorophenyl-piperidin-4-ylidene-methyl)-benzamide hydrochloride salt.

We find that a first polymorph (exemplified as "Polymorph A" in the Examples) N,N-diethyl-4-(3-fluorophenyl-piperidin-4-ylidene-methyl)-benzamide hydrochloride salt may be produced using a process described below.

Therefore, one aspect of the invention provides a process of preparing the first polymorph of N,N-diethyl-4-(3-fluorophenyl-piperidin-4-ylidene-methyl)-benzamide hydrochloride salt.

In one embodiment, the process of preparing the first polymorph of N,N-diethyl-4-(3-fluorophenyl-piperidin-4-ylidene-methyl)-benzamide hydrochloride salt includes:

dissolving N,N-diethyl-4-(3-fluorophenyl-piperidin-4-ylidene-methyl)-benzamide hydrochloride salt and a solvent selected from isopropanol, butanol and acetone at a first predetermined temperature to form a solution; and cooling down said solution to a second predetermined temperature whereby at least a portion of said N,N-diethyl-4-(3-fluorophenyl-piperidin-4-ylidene-methyl)-benzamide hydrochloride salt crystallizes, wherein said first predetermined temperature is at least 10° C. higher than said second predetermined temperature.

In another embodiment, the solvent used in the process of preparing the first polymorph is isopropanol.

In a further embodiment, the first predetermined temperature used in the process of preparing the first polymorph is between 60° C. and 80° C.

In an even further embodiment, the second predetermined temperature used in the process of preparing the first polymorph is between 0° C. and 40° C.

In a further embodiment, the process of preparing the first polymorph further includes the step of:

filtering said solution after the step of cooling down to separate a solid portion.

In a further embodiment, the process of preparing the first polymorph further includes the step of:

drying said solid portion.

In another aspect, an embodiment of the invention provides a crystalline polymorph of N,N-diethyl-4-(3-fluorophenyl-piperidin-4-ylidene-methyl)-benzamide hydrochloride salt, wherein said polymorph has a proton relaxation time less than 6 seconds when said relaxation time is measured using a solid state NMR probe at an ambient temperature.

Another embodiment of the invention provides a crystalline polymorph of N,N-diethyl-4-(3-fluorophenyl-piperidin-4-ylidene-methyl)-benzamide hydrochloride salt, wherein solid state $^{13}C$ NMR spectrum of said polymorph has a peak at a chemical shift between 43 ppm and 45 ppm when tetramethylsilane is used as a standard, wherein said spectrum is acquired at ambient temperature using a solid state NMR probe spinning at 10 KHz.

A further embodiment of the invention provides a crystalline polymorph of N,N-diethyl-4-(3-fluorophenyl-piperidin-4-ylidene-methyl)-benzamide hydrochloride salt, wherein solid state $^{13}C$ NMR spectrum of said polymorph has a peak at a chemical shift between 168 ppm and 170 ppm when tetramethylsilane is used as a standard, wherein said spectrum is acquired at ambient temperature using a solid state NMR probe spinning at 10 KHz.

An even further embodiment of the invention provides a crystalline polymorph of N,N-diethyl-4-(3-fluorophenyl-piperidin-4-ylidene-methyl)-benzamide hydrochloride salt, wherein said polymorph has a fluorine-19 relaxation time less than 30 seconds when said relaxation time is measured using a solid state NMR probe at an ambient temperature.

In one embodiment, the above-identified crystalline polymorph may be prepared using one or more processes described above.

We further find that the first polymorph can be converted into a second polymorph (exemplified as "Polymorph B" in the Examples) of N,N-diethyl-4-(3-fluorophenyl-piperidin-4-ylidene-methyl)-benzamide hydrochloride salt using a suitable process.

Therefore, another aspect of the invention provides a process of preparing the second polymorph of N,N-diethyl-4-(3-fluorophenyl-piperidin-4-ylidene-methyl)-benzamide hydrochloride salt.

In one embodiment, the process of preparing the second polymorph of N,N-diethyl-4-(3-fluorophenyl-piperidin-4-ylidene-methyl)-benzamide hydrochloride salt includes:

combining N,N-diethyl-4-(3-fluorophenyl-piperidin-4-ylidene-methyl)-benzamide hydrochloride salt and a solvent selected from isopropanol, butanol and acetone at a temperature between 20° C. and 80° C. for at least one hour, wherein said N,N-diethyl-4-(3-fluorophenyl-piperidin-4-ylidene-methyl)-benzamide hydrochloride salt and said solvent are combined at a predetermined ratio whereby a portion of said N,N-diethyl-4-(3-fluorophenyl-piperidin-4-ylidene-methyl)-benzamide hydrochloride salt remains to be solid at said temperature in the combination.

In another embodiment, the process of preparing the second polymorph includes the step of combining N,N-diethyl-4-(3-fluorophenyl-piperidin-4-ylidene-methyl)-benzamide hydrochloride salt and a solvent selected from isopropanol and acetone at a temperature of about 50° C. for at least one hour.

In a further embodiment, the process of preparing the second polymorph includes the steps of:

combining N,N-diethyl-4-(3-fluorophenyl-piperidin-4-ylidene-methyl)-benzamide hydrochloride salt and a solvent selected from isopropanol, butanol and acetone at a temperature between 20° C. and 80° C.;

cooling down or maintaining the combination to a temperature of less than 35° C.; and filtering the combination.

In an even further embodiment, the process of preparing the second polymorph includes the steps of:

combining N,N-diethyl-4-(3-fluorophenyl-piperidin-4-ylidene-methyl)-benzamide hydrochloride salt and a solvent selected from isopropanol, butanol and acetone at a temperature between 20° C. and 80° C.; and seeding the combination with a polymorph of N,N-diethyl-4-(3-fluorophenyl-piperidin-4-ylidene-methyl)-benzamide hydrochloride salt having a proton relaxation time between 6 and 10 seconds when said relaxation time is measured using a solid state NMR probe at an ambient temperature.

In yet a further embodiment, the process of preparing the second polymorph includes the step of combining N,N-diethyl-4-(3-fluorophenyl-piperidin-4-ylidene-methyl)-benzamide hydrochloride salt and isopropanol at a temperature between 20° C. and 80° C.

In an even further embodiment, the process of preparing the second polymorph includes the step of heating N,N-diethyl-4-(3-fluorophenyl-piperidin-4-ylidene-methyl)-benzamide hydrochloride salt to a temperature between 215° C. and 235° C.

Accordingly, in another aspect, an embodiment of the invention provides a second polymorph of N,N-diethyl-4-(3-fluorophenyl-piperidin-4-ylidene-methyl)-benzamide hydrochloride salt, wherein said polymorph has a proton relaxation time between 6 and 10 seconds when said relaxation time is measured using a solid state NMR probe at an ambient temperature.

Another embodiment of the invention provides a second polymorph of N,N-diethyl-4-(3-fluorophenyl-piperidin-4-ylidene-methyl)-benzamide hydrochloride salt, wherein solid state $^{13}$C NMR spectrum of said polymorph has at least one peak at a chemical shift between 41 ppm and 43 ppm when tetramethylsilane is used as a standard, wherein said spectrum is acquired at ambient temperature using a solid state NMR probe spinning at 10 KHz.

A further embodiment of the invention provides a second polymorph of N,N-diethyl-4-(3-fluorophenyl-piperidin-4-ylidene-methyl)-benzamide hydrochloride salt, wherein solid state $^{13}$C NMR spectrum of said polymorph has at least one peak at a chemical shift between 170 ppm and 175 ppm when tetramethylsilane is used as a standard, wherein said spectrum is acquired at ambient temperature using a solid state NMR probe spinning at 10 KHz.

An even further embodiment of the invention provides a second polymorph of N,N-diethyl-4-(3-fluorophenyl-piperidin-4-ylidene-methyl)-benzamide hydrochloride salt, wherein said polymorph has a fluorine-19 relaxation time between 30 and 50 seconds when said relaxation time is measured using a solid state NMR probe at an ambient temperature.

The second polymorph of N,N-diethyl-4-(3-fluorophenyl-piperidin-4-ylidene-methyl)-benzamide hydrochloride salt according to one or more embodiments of the invention described above may be prepared using one or more of the processes of preparing the second polymorph described above.

An even further embodiment of the invention provides a polymorph of N,N-diethyl-4-(3-fluorophenyl-piperidin-4-ylidene-methyl)-benzamide hydrochloride salt, wherein said polymorph has a melting point of at least 210° C.

An even further embodiment of the invention provides a polymorph of N,N-diethyl-4-(3-fluorophenyl-piperidin-4-ylidene-methyl)-benzamide hydrochloride salt, wherein said polymorph has a melting point of at least 230° C.

A further aspect of the invention provides a combination of the first polymorph and the second polymorph.

In one embodiment, the combination of the first polymorph and the second polymorph may exist as a mixture of these two polymorphs.

The polymorph (e.g., Polymorphs A or B shown in the Examples) are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

The polymorphs are useful as an immunomodulator, especially for autoimmune diseases, such as arthritis, for skin grafts, organ transplants and similar surgical needs, for collagen diseases, various allergies, for use as anti-tumour agents and anti-viral agents.

The polymorphs are useful for the treatment of disease states where degeneration or dysfunction of opioid receptors is present or implicated in that paradigm. This may involve the use of isotopically labelled versions of the polymorph in diagnostic techniques and imaging applications such as positron emission tomography (PET).

The polymorphs are useful for the treatment of diarrhoea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

The polymorphs are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of the polymorphs for the manufacture of a medicament for the treatment of any of the conditions discussed above.

A further aspect of the invention is a method for the treatment of a subject suffering from any of the conditions discussed above, whereby an effective amount of the polymorphs is administered to a patient in need of such treatment.

Thus, the invention provides a polymorph as hereinbefore defined for use in therapy.

In a further aspect, the invention provides the use of a polymorph as hereinbefore defined in the manufacture of a medicament for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The polymorphs are useful in therapy, especially for the therapy of various pain conditions including, but not limited to: chronic pain, neuropathic pain, acute pain, back pain, cancer pain, and visceral pain.

In use for therapy in a warm-blooded animal such as a human, the polymorphs may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the polymorph, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided polymorph. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the polymorph, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of a polymorph as defined above for the manufacture of a medicament.

Also within the scope of the invention is the use of the polymorph for the manufacture of a medicament for the therapy of pain and/or anxiety.

Additionally provided is the use of the polymorph for the manufacture of a medicament for the therapy of various pain conditions including, but not limited to: chronic pain, neuropathic pain, acute pain, back pain, cancer pain, and visceral pain.

A further aspect of the invention is a method for therapy of a subject suffering from any of the conditions discussed above, whereby an effective amount of the polymorphs is administered to a patient in need of such therapy.

Additionally, there is provided a pharmaceutical composition comprising at least one of the polymorphs in association with a pharmaceutically acceptable carrier.

Particularly, there is provided a pharmaceutical composition comprising at least one of the polymorphs in association with a pharmaceutically acceptable carrier for therapy, more particularly for therapy of pain.

Further, there is provided a pharmaceutical composition comprising at least one of the polymorphs in association with a pharmaceutically acceptable carrier use in any of the conditions discussed above.

EXAMPLES

The invention will further be described in more detail by the following Examples which describe methods whereby compounds of the present invention may be prepared, purified, analyzed and biologically tested, and which are not to be construed as limiting the invention.

Example 1

Preparation of Polymorph A of N,N-Diethyl-4-(3-Fluorophenyl-Piperidin-4-Ylidene-Methyl)-Benzamide Hydrochloride Salt Charge 24.62 g of N,N-diethyl-4-(3-fluorophenyl-piperidin-4-ylidene-methyl)-benzamide hydrochloride salt (prepared using a method of U.S. Pat. No. 6,187,792 to Delorme et al. or a method substantially similar thereto) to Vessel 1.

Vessel 1 is a 150 ml round bottomed flask equipped with overhead stirrer, condenser and thermometer.

Add isopropanol (78 ml) to Vessel 1 at ambient temperature.

Commence agitation.

Heat the contents of Vessel 1 to 70° C.

Hold the contents of Vessel 1 at 70° C. until full dissolution is apparent.

Filter the batch through an in-line filter into Vessel 2.

Vessel 2 is a 150 ml round bottomed flask equipped with overhead stirrer, condenser and thermometer.

Add isopropanol (5 ml) to Vessel 1.

Filter the line wash through the in-line filter into Vessel 2.

Commence agitation in Vessel 2.

Cool the solution to 0° C. over at least 1 hour.

A thick white slurry is formed.

Hold the mixture at 0° C. for at least 1 hour.

Transfer the contents of Vessel 2 to the filter and deliquor thoroughly.

Add pre-chilled isopropanol (12 ml) to Vessel 2.

Transfer the contents of Vessel 2 to the filter and deliquor thoroughly.

Discharge the solid product and dry the solid under vacuum (60° C., 250 mbar) for at least 18 hours.

It yields 20.81 g (88.4%). XRD confirms the isolated solid to be Polymorph A as shown in FIG. 1.

Example 2

Preparation of Polymorph B of N,N-Diethyl-4-(3-Fluorophenyl-Piperidin-4-Ylidene-Methyl)-Benzamide Hydrochloride Salt Charge 64.5 grams of Polymorph A as prepared in Example 1 to Vessel 1.

Vessel 1 is a 500 ml jacketed vessel equipped with overhead stirrer, thermometer, Lasentec probe and inert gas inlet.

Charge 2-propanol (203 ml) to Vessel 1.

Heat the contents of Vessel 1 to 80° C.

Hold the contents of Vessel 1 for 1 hour.

All the solids dissolve during this time

Transfer the contents of Vessel 1 to Vessel 2 via an in-line filter.

Vessel 2 is equipped identically to Vessel 1.

A 9 cm split Buchner funnel was used as filter. Alternative filter tools may be used.

Charge 2-propanol (13 ml) to Vessel 1.

Transfer the contents of Vessel 1 into Vessel 2 via the in-line filter.

Cool the contents of Vessel 2 to 35° C.

Hold the contents of Vessel 2 for 1 hour.

Crystallisation occurs during this period otherwise the hold should be extended until the onset of crystallisation.

Warm the contents of Vessel 2 to 50° C.

Hold the contents of Vessel 2 for 8 hours.

Polymorphic transformation of the slurry occurs during this hold

Cool the contents of Vessel 2 to 40° C.

Hold the contents of Vessel 2 for 30 minutes.

Cool the contents of Vessel 2 to 30° C.

Hold the contents of Vessel 2 for 30 minutes.

Cool the contents of Vessel 2 to 20° C.

Hold the contents of Vessel 2 for 30 minutes.

Cool the contents of Vessel 2 to 0° C.

Hold the contents of Vessel 2 for 2 hours

Transfer the contents of Vessel 2 to filtration apparatus

A 9 cm split Buchner funnel was used.

Deliquor the wet filter cake.

Charge 2-propanol (32 ml) to Vessel 2.

Cool the contents of Vessel 2 to 0° C.

Transfer the contents of Vessel 2 to the filter.

Deliquor the filter cake.

Dry the wet cake in a vacuum oven

The vacuum oven used 50° C. at 200 mbar vacuum.

XRD confirms the isolated solid to be exclusively Polymorph B as shown in FIG. 1.

Example 3

Preparation of polymorph B of N,N-Diethyl-4-(3-Fluorophenyl-Piperidin-4-Ylidene-Methyl)-Benzamide Hydrochloride Salt Via a Seeding Protocol Charge Polymorph A of N,N-diethyl-4-(3-fluorophenyl-piperidin-4-ylidene-methyl)-benzamide hydrochloride salt (45.0 g) to Vessel 1

Vessel 1 is a 500 ml jacketed reactor fitted with retreat curve stirrer, inert gas inlet, thermometer and Lasentec probe Charge 2-propanol (320 ml) to Vessel 1

Heat the contents of Vessel 1 to 49° C. to dissolve all solids.

At lower temperatures, significant solids remain suspended

Cool the contents of Vessel 1 cooled to 40° C.

10 mg of polymorph B as made in Example 2 is charged to Vessel 1.

Contents held at 40° C. for 4 hours

The onset of crystallisation occurs during this period

Contents of Vessel 1 were warmed to 45° C.

The batch was held overnight at this stage

Contents of Vessel 1 cooled from 45° C. to 40° C. over a period of 1 hour

Contents of Vessel 1 held at 40° C. for 1 hour.

Contents of Vessel 1 cooled to 30° C. over 1 hour

Contents of Vessel 1 held at 30° C. for 1 hour.

Contents of Vessel 1 cooled to 20° C. over 1 hour

Contents of Vessel 1 held at 20° C. for 1 hour.

Solids collected by filtration and air-dried.

The weight of the isolated solid is 18.22 g. The XRD of the solid confirms that the is solid contains exclusively polymorph B (as shown in FIG. 1).

Example 4

Solid State NMR Characterization of Polymorphs A and B

The solid state NMR was carried out using a 4 mm HX probe on a Bruker WB400 NMR instrument at room temperature (27° C.). A cross-polarisation pulse sequence (contact time being 1 ms) is used during the acquisition. $^{13}$C is decoupled from protons (frequency 399.87 MHz) and the probe is spinning at 10 KHz. The following parameters (shown in Table 1) are used during the experiment.

TABLE 1

| Parameter | Value |
| --- | --- |
| Acquisition Time(sec) | 0.1327 |
| Frequency (MHz) | 100.55 |
| Nucleus | 13C |
| Number of transients | 8000 |
| relaxation delay (sec) | 8 |
| Spectrum offset (Hz) | 10149.3164 |
| Sweep Width (Hz) | 30856.56 |

Figure 2:
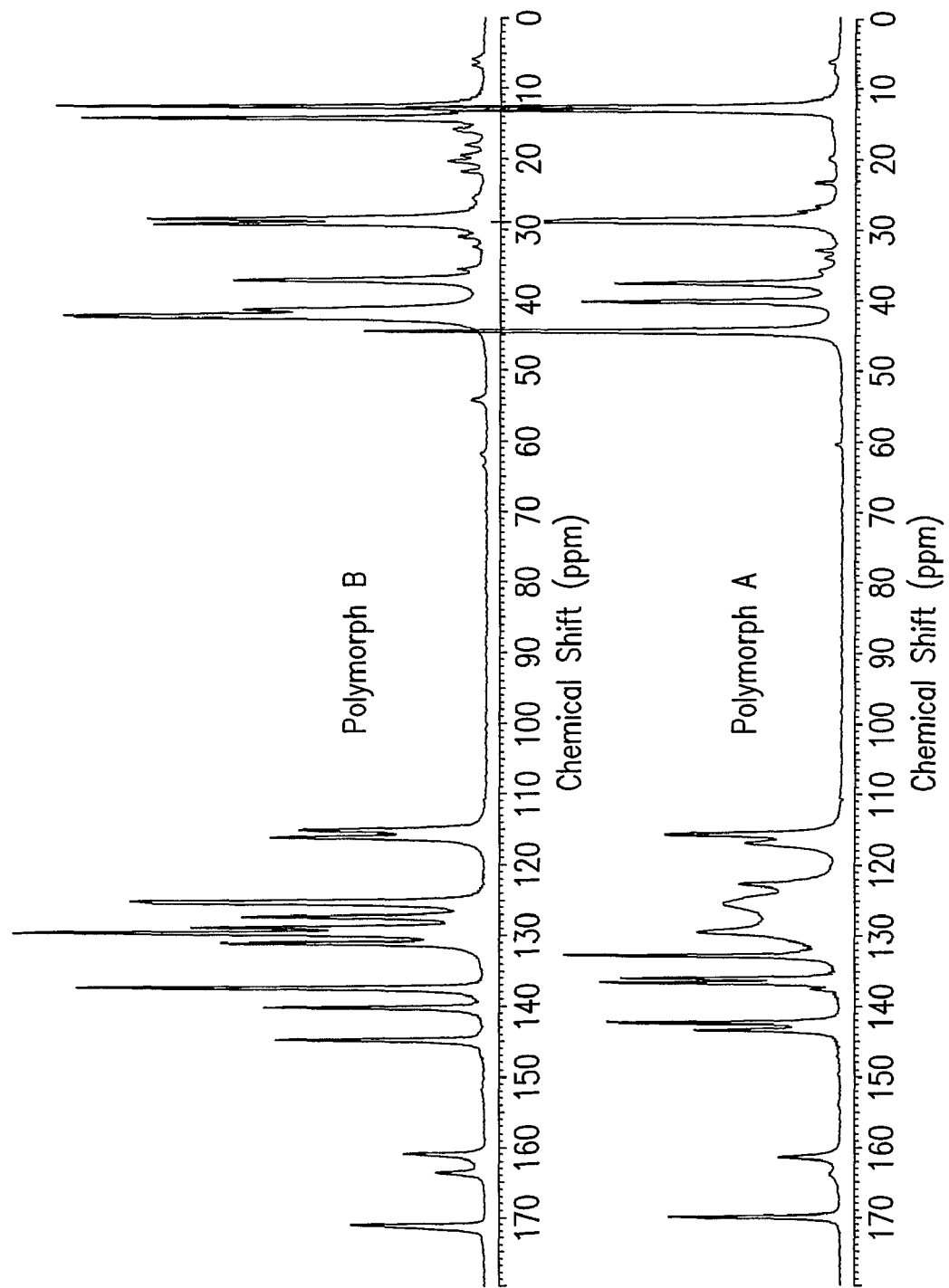
FIG. 2 shows the solid state $^{13}C$ NMR of Polymorphs A and B.

The $^{13}$C solid state NMR spectra for both Polymorphs A and B are obtained and shown in FIG. 2.

Table 2 lists the peaks in these spectra.

TABLE 2

| | polymorph A | | | | polymorph B | | |
| --- | --- | --- | --- | --- | --- | --- | --- |
| No. | (ppm) | (Hz) | Height | No. | (ppm) | (Hz) | Height |
| 1 | 12.4 | 1246.5 | 0.7517 | 1 | 12.66 | 1273 | 0.9087 |
| 2 | 12.85 | 1291.7 | 0.7465 | 2 | 14.28 | 1435.8 | 0.8525 |
| 3 | 28.43 | 2859 | 0.8219 | 3 | 28.44 | 2859.9 | 0.7134 |
| 4 | n/a | n/a | n/a | 4 | 29.17 | 2933.2 | 0.7011 |
| 5 | 37.35 | 3755.7 | 0.4483 | 5 | 37.18 | 3738.8 | 0.5325 |
| 6 | 39.97 | 4019.4 | 0.5123 | 6 | 41.39 | 4162 | 0.5136 |
| 7 | 44.1 | 4433.9 | 1 | 7 | 42.28 | 4251.5 | 0.8939 |
| 8 | 115.37 | 11599.8 | 0.3784 | 8 | 115.29 | 11592 | 0.392 |
| 9 | 116.49 | 11712.9 | 0.263 | 9 | 116.26 | 11689.7 | 0.4535 |
| 10 | 122.48 | 12315.7 | 0.2735 | 10 | 125.32 | 12601.1 | 0.7512 |
| 11 | 125.48 | 12617.1 | 0.3164 | 11 | 127.51 | 12820.8 | 0.5156 |
| 12 | 129.08 | 12978.8 | 0.3797 | 12 | 129.05 | 12975.5 | 0.6215 |
| 13 | 132.53 | 13325.4 | 0.4176 | 13 | 129.78 | 13048.7 | 1 |
| 14 | 135.75 | 13649.4 | 0.3817 | 14 | 131.23 | 13195.2 | 0.5571 |
| 15 | 136.2 | 13694.6 | 0.3875 | 15 | 137.63 | 13838.1 | 0.8646 |
| 16 | 142.04 | 14282.4 | 0.3424 | 16 | 140.38 | 14114.8 | 0.4675 |
| 17 | 142.94 | 14372.8 | 0.2648 | 17 | 144.99 | 14578.7 | 0.4401 |
| 18 | 160.93 | 16181.2 | 0.1016 | 18 | 161.1 | 16198.1 | 0.1627 |
| 19 | 163.4 | 16429.9 | 0.0131 | 19 | 163.69 | 16458.5 | 0.0901 |
| 20 | 169.77 | 17070.4 | 0.2515 | 20 | 171.3 | 17223.5 | 0.2787 |

Figure 4:
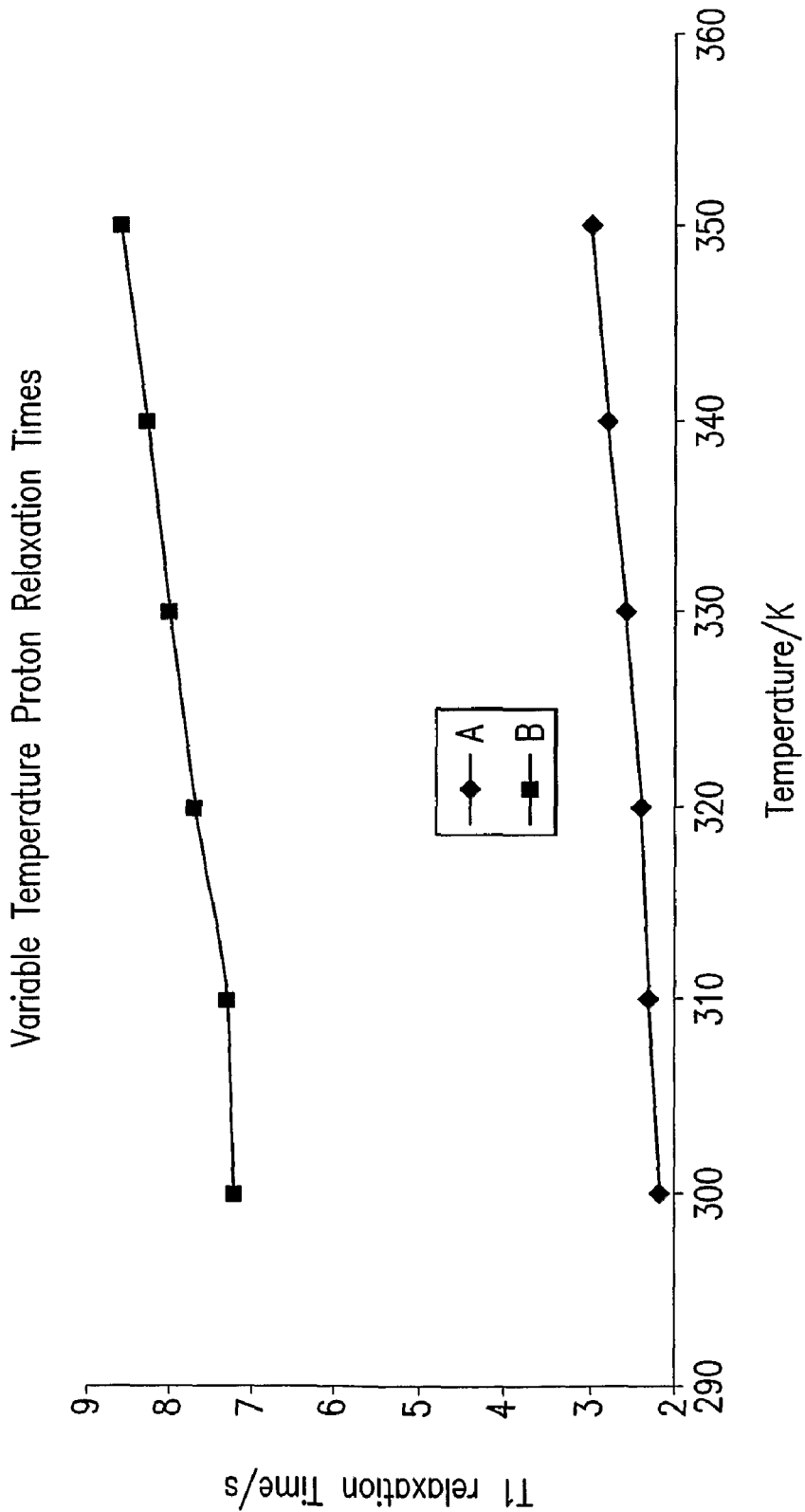
FIG. 4 illustrates the temperature dependency of relaxation times of $^1H$ of Polymorphs A and B (labelled as "A" and "B," respectively).

Relaxation times (T1) for both $^1$H and $^{19}$F have been measured. At ambient temperature, the relaxation time of $^1$H and $^{19}$F for both the polymorphs A and B are shown in FIG. 3. The temperature dependency of the relaxation time of $^1$H for these polymorphs is also investigated. The results are summarized in FIG. 4.

Example 5

Solubility of Polymorphs A and B

From a well-mixed slurry of Polymorph B and isopropanol (with the agitator being stopped), a known volume of the liquors is drawn off using a pipette and transferred to a volumetric flask, which is left in the fume cupboard for the solvent to evaporate. The temperature at which the sample is taken is noted, and after a day any remaining solvent is blown off with nitrogen and then transferred to a vacuum oven. The solubility samples are dried in the vacuum oven at around 40° C. and weighed until their mass is constant, indicating that there is only solid left. The solubility of Polymorph B is determined based on the measured weights of the samples.

In order to obtain a solubility curve and meta-stable zone (clear and cloud curves) for Polymorph A in isopropanol an experiment is set up using the turbidity probe equipment. The setup and operation of which is described in detail by A. R. Parsons, S. N. Black and R. Colling., 2003, Automated measurement of metastable zones for pharmaceutical compounds, Trans IChenE, Part A, 81: 700-704, which is incorporated by reference herein in its entirety.

Figure 5:
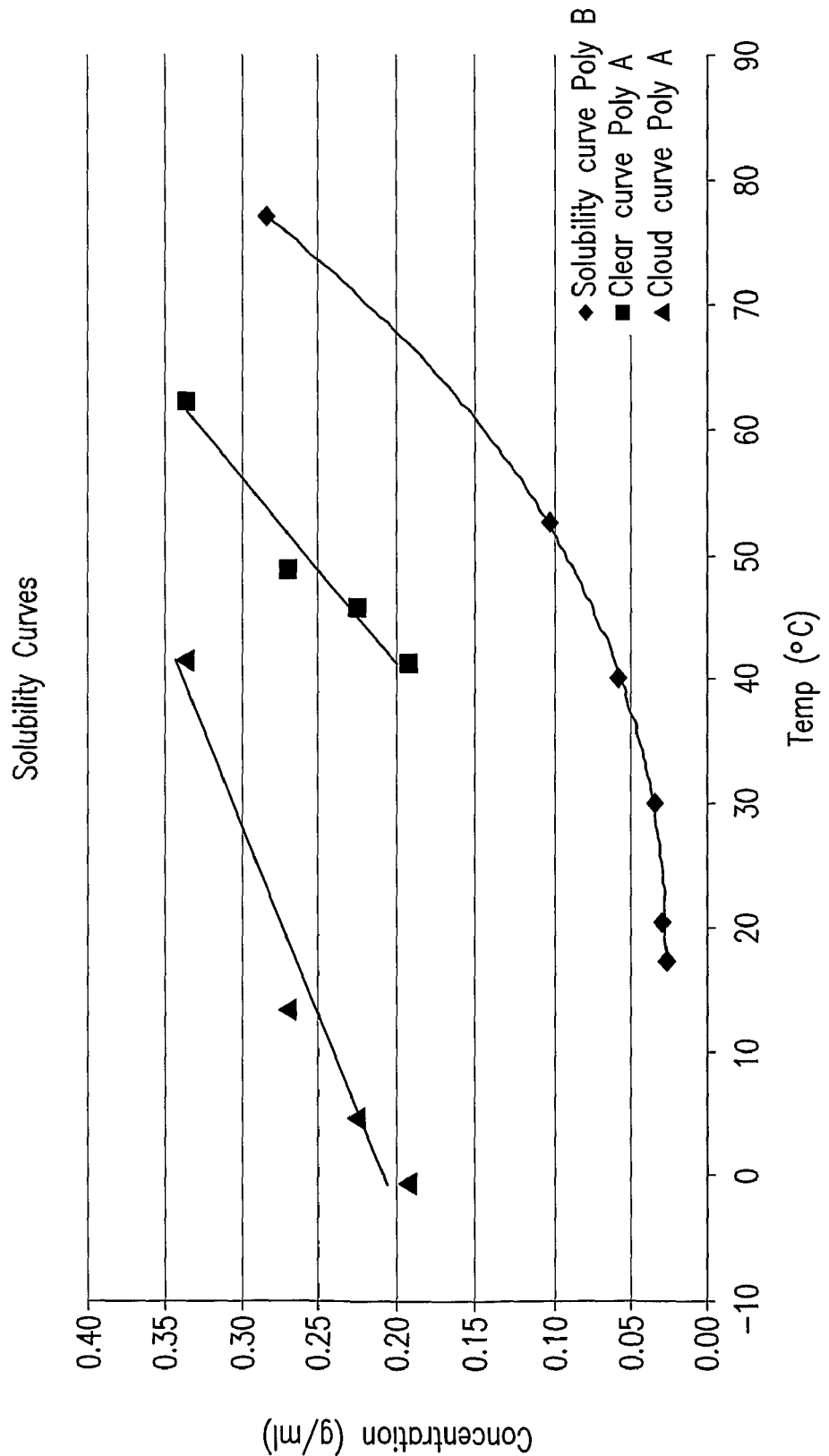
FIG. 5 illustrates the solubility curves of Polymorphs A and B (labelled as "Poly A" and "Poly B," respectively).

The results are shown in FIG. 5. Based on these results, it is clear that Polymorph B is less soluble than Polymorph A at low temperatures. It is also found that Polymorph B is more stable than Polymorph A at a temperature range between 20° C. and 80° C.

Example 6

DSC Experiments for Polymorphs A and B

Figure 6A:
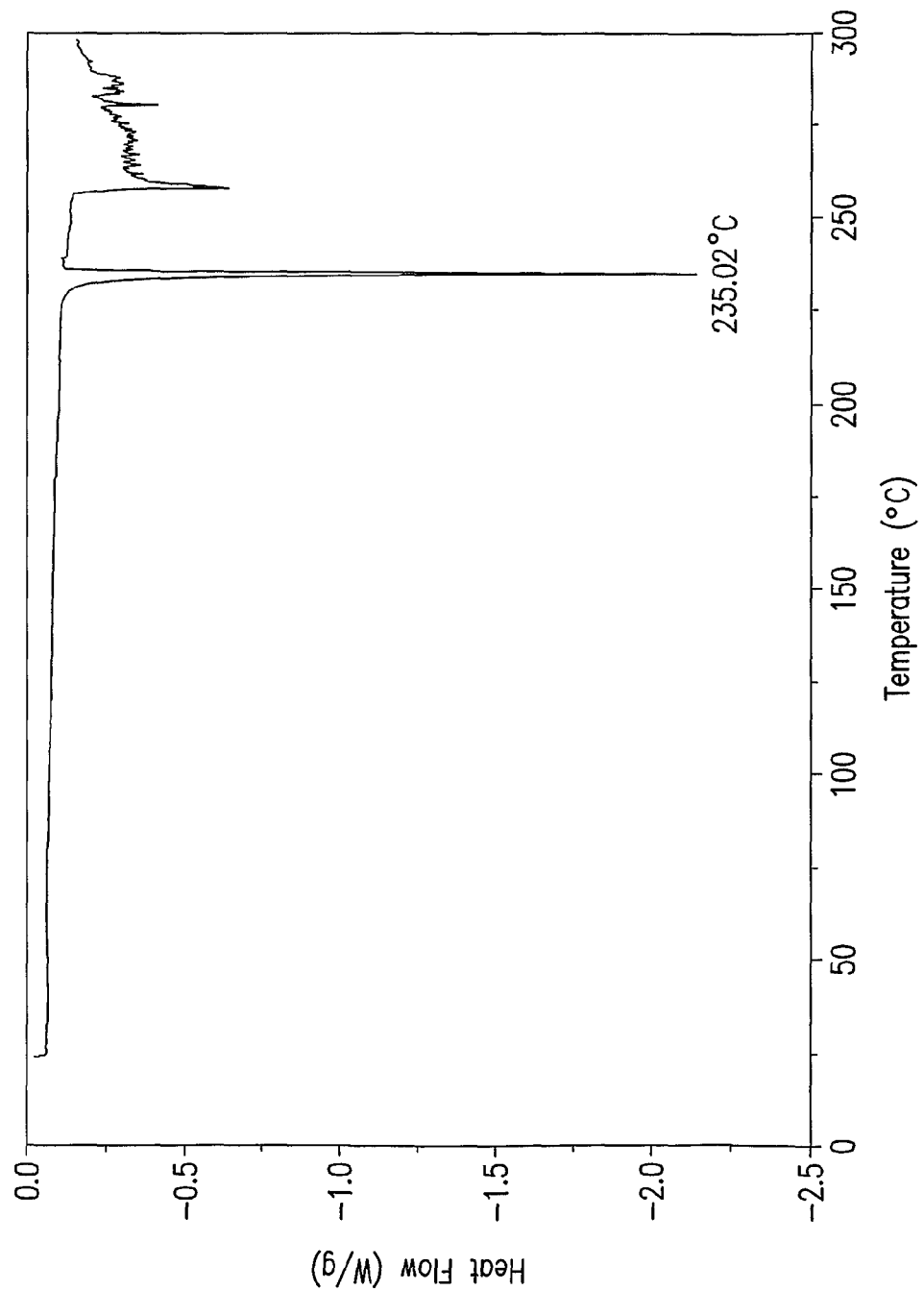
FIG. 6A shows the DSC traces of Polymorph A.
Figure 6B:
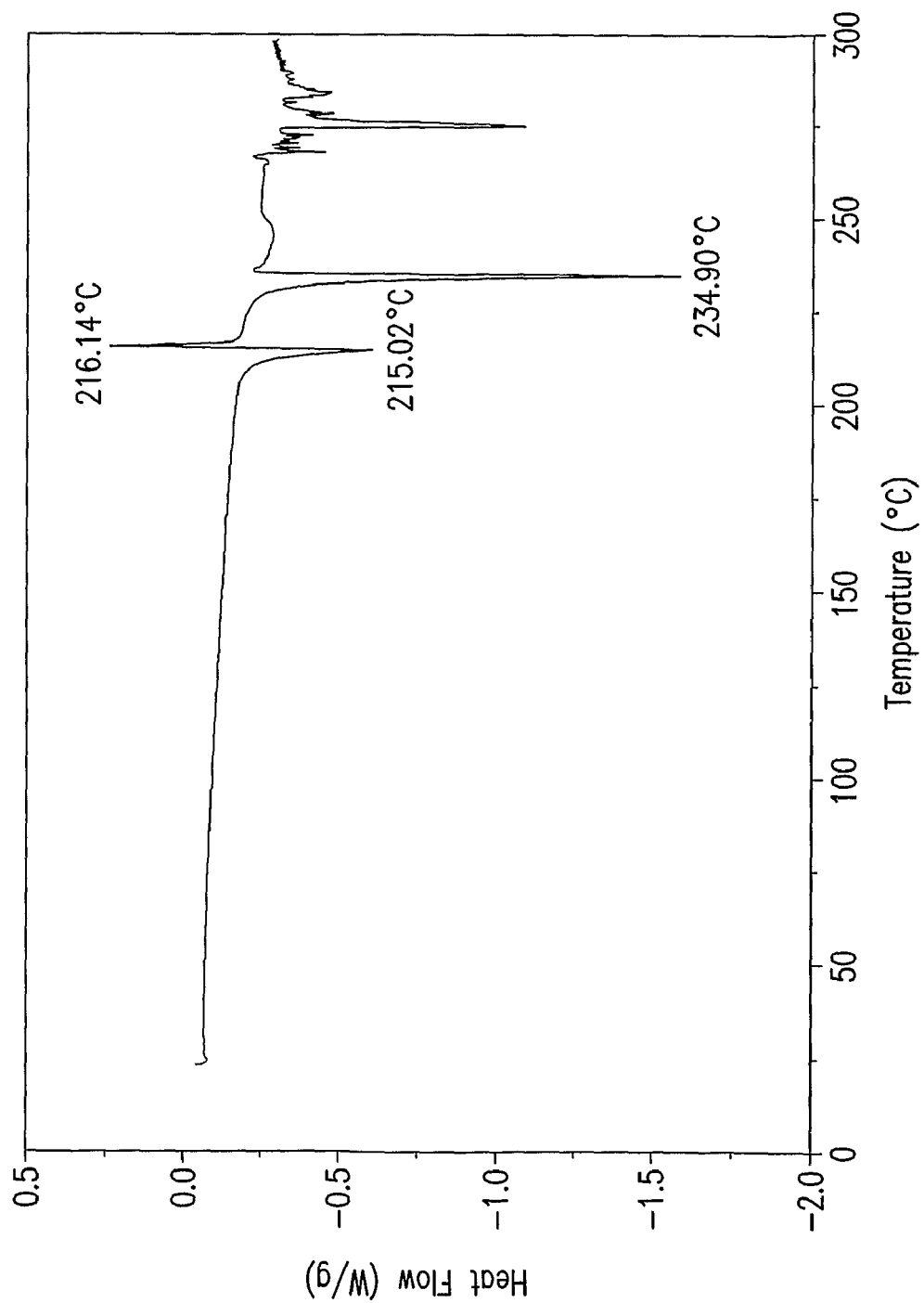
FIG. 6B shows the DSC traces of Polymorph B

Differential Scanning Calorimetry (DSC) is carried out for both Polymorphs A and B at a temperature ramping rate of 2° C./minute under a nitrogen atmosphere. The results are shown in FIG. 6A and FIG. 6B, respectively. As shown in FIG. 6A, Polymorph A has an endothermic event due to its melting at about 235° C. The DSC of Polymorph B in FIG. 6B suggests a melt at about 215° C. followed by a recrystallization at about 216° C. The recrystallized form of Polymorph B then melts at about 235° C., the same temperature as the Polymorph A melts, suggesting the this recrystallized form is Polymorph A.

We claim:

1. Polymorph A of N,N-diethyl-4-(3-fluorophenyl-piperidin-4-ylidene-methyl)-benzamide hydrochloride salt, said polymorph A having a $^{13}$C solid state NMR spectrum substantially as shown in FIG. 2.

2. Polymorph B of N,N-diethyl-4-(3-fluorophenyl-piperidin-4-ylidene-methyl)-benzamide hydrochloride salt, said polymorph B having a $^{13}$C solid state NMR spectrum substantially as shown in FIG. 2.

3. Polymorph A of N,N-diethyl-4-(3-fluorophenyl-piperidin-4-ylidene-methyl)-benzamide hydrochloride salt as claimed in claim 1, prepared by a process comprising:
    combining N,N-diethyl-4-(3-fluorophenyl-piperidin-4-ylidene-methyl)-benzamide hydrochloride salt and a solvent selected from the group consisting of isopropanol, butanol and acetone at a temperature between 20° C. and 80° C.;
    warming said N,N-diethyl-4-(3-fluorophenyl-piperidin-4-ylidene-methyl)-benzamide hydrochloride salt and solvent to at least 50° C. for at least one hour to achieve a solution;
    cooling said solution to a temperature of less than 35° C. to achieve crystallization of said N,N-diethyl-4-(3-fluorophenyl-piperidin-4-ylidene-methyl)-benzamide hydrochloride salt;
    optionally seeding said solution with a polymorph A seed; and
    recovering said crystallized polymorph A.

4. The polymorph of claim 3, prepared by a process wherein said solvent is isopropanol.

5. Polymorph B of N,N-diethyl-4-(3-fluorophenyl-piperidin-4-ylidene-methyl)-benzamide hydrochloride salt, as claimed in claim 2, prepared by a process comprising:
    combining N,N-diethyl-4-(3-fluorophenyl-piperidin-4-ylidene-methyl)-benzamide hydrochloride salt and a solvent selected from the group consisting of isopropanol, butanol and acetone at a temperature between 20° C. and 80° C.;

warming said N,N-diethyl-4-(3-fluorophenyl-piperidin-4-ylidene-methyl)-benzamide hydrochloride salt and solvent to at least 50° C. for at least one hour to achieve a solution;

cooling said solution to a temperature of less than 35° C. to achieve crystallization of said N,N-diethyl-4-(3-fluorophenyl-piperidin-4-ylidene-methyl)-benzamide hydrochloride salt;

optionally seeding said solution with a polymorph B seed; and recovering said crystallized polymorph B.

6. The polymorph of claim 5, prepared by a process wherein said solvent is isopropanol.

7. A pharmaceutical composition comprising a polymorph according to claim 1 and a pharmaceutically acceptable carrier.

8. A pharmaceutical composition comprising a polymorph according to claim 2 and a pharmaceutically acceptable carrier.

9. A method for the treatment of pain in a warm-blooded animal, comprising the step of administering to said animal in need of such treatment a therapeutically effective amount of a pharmaceutical composition according to claim 7.

10. A method for the treatment of anxiety in a warm-blooded animal, comprising the step of administering to said animal in need of such treatment a therapeutically effective amount of a pharmaceutical composition according to claim 7.

11. A method for the treatment of pain in a warm-blooded animal, comprising the step of administering to said animal in need of such treatment a therapeutically effective amount of a pharmaceutical composition according to claim 8.

12. A method for the treatment of anxiety in a warm-blooded animal, comprising the step of administering to said animal in need of such treatment a therapeutically effective amount of a pharmaceutical composition according to claim 8.

* * * * *